United States Patent [19]

Pagratis et al.

[11] Patent Number: 5,846,713
[45] Date of Patent: Dec. 8, 1998

[54] HIGH AFFINITY HKGF NUCLEIC ACID LIGANDS AND INHIBITORS

[75] Inventors: Nikos Pagratis; Larry Gold, both of Boulder, Colo.

[73] Assignee: Nexstar Pharmaceuticals, Inc., Boulder, Colo.

[21] Appl. No.: 465,594

[22] Filed: Jun. 5, 1995

Related U.S. Application Data

[63] Continuation-in-part of Ser. No. 714,131, Jun. 10, 1991, Pat. No. 5,475,096, Ser. No. 931,473, Aug. 17, 1992, Pat. No. 5,270,163, Ser. No. 964,624, Oct. 21, 1992, Pat. No. 5,496, 938, and Ser. No. 117,991, Sep. 8, 1993, abandoned, said Ser. No. 714,131, is a continuation-in-part of Ser. No. 536,428, Jun. 11, 1990, abandoned.

[51] Int. Cl.$^6$ .............................. C12Q 1/68; C12P 19/34; C07H 21/04; C07H 21/02
[52] U.S. Cl. .......................... 435/6; 435/91.2; 536/25.4; 935/77; 935/78
[58] Field of Search ..................... 435/6, 91.2; 536/25.4; 935/77, 78

[56] References Cited

U.S. PATENT DOCUMENTS 5,459,015  10/1995  Janjic et al. ................................ 435/6

FOREIGN PATENT DOCUMENTS

| 2 183 661 | 6/1987 | United Kingdom . |
| WO 89/06694 | 7/1989 | WIPO . |
| 9214843 | 9/1992 | WIPO ........................................ 435/6 |
| WO 94/25057 | 11/1994 | WIPO . |

OTHER PUBLICATIONS

Joyce (1989) Gene 82:83.
Joyce and Inoue (1989) Nucleic Acids Research 17:711.
Ellington and Szostak (1990) Abstract of paper presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Olliphant et al. (1986) Gene 44:177.
Robertson and Joyce (1990) Nature 344:467.
Thiesen and Bach (1990) Nucleic Acids Research 18:3203.
Alarid et al. (1994) Proc. Natl. Acad. Sci. USA 91:1074.
Bottaro et al. (1993) J. Biol. Chem. 268:9180.
R&D Systems, Specification Sheet For Anti–Human FGF–7/KGF Neutralizing Antibody, dated Feb. 1, 1995.

*Primary Examiner*—Stephanie W. Zitomer
*Attorney, Agent, or Firm*—Swanson & Bratschun LLC

[57] ABSTRACT

Methods are described for the identification and preparation of high-affinity nucleic acid ligands to hKGF. Included in the invention are specific RNA ligands to hKGF identified by the SELEX method. Also included are RNA ligands that inhibit the interaction of hKGF with its receptor.

6 Claims, 3 Drawing Sheets

SEQUENCE LISTING ( 1 ) GENERAL INFORMATION:

( i i i ) NUMBER OF SEQUENCES: 77

( 2 ) INFORMATION FOR SEQ ID NO: 1:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 1:

```
GGGAGGACGA  UGCGGNNNNN  NNNNNNNNNN  NNNNNNNNNN  NNNNNNNNNN        50
NNNNNCAGAC  GACUCGCCCG  A                                         71
```

( 2 ) INFORMATION FOR SEQ ID NO: 2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 2:

```
TAATACGACT  CACTATAGGG  AGGACGATGC  GG                            32
```

( 2 ) INFORMATION FOR SEQ ID NO: 3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 3:

```
TCGGGCGAGT  CGTCTG                                                16
```

( 2 ) INFORMATION FOR SEQ ID NO: 4:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 4:

```
GGGAGGACGA  UGCGGGAAGG  GACGAUAAAG  AGGAAUCGAA  CAACAAGUGG        50
CUGGCCAGAC  GACUCGCCCG  A                                         71
```

( 2 ) INFORMATION FOR SEQ ID NO: 5:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 5:

GGGAGGACGA UGCGGGCGGG AAGGUCCGAA GACCGGCGAA AGGAACGAGA     50

UUGCCCAGAC GACUCGCCCG A     71

( 2 ) INFORMATION FOR SEQ ID NO: 6:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 6:

GGGAGGACGA UGCGGGUGGU GAAGAGGUAC CGGAAUUGCU AAAGAUACCA     50

CGGCCCAGAC GACUCGCCCG A     71

( 2 ) INFORMATION FOR SEQ ID NO: 7:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 7:

GGGAGGACGA UGCGGGCAGG GAGCAAUGAA CUCAAGUCAA GCCGGUGCAC     50

GUGGGCAGAC GACUCGCCCG A     71

( 2 ) INFORMATION FOR SEQ ID NO: 8:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 8:

GGGAGGACGA UGCGGUAGCU GCUGUCAUGC AAGACACUAG AAGAUUAAGA     50

UGGGGCAGAC GACUCGCCCG A     71

( 2 ) INFORMATION FOR SEQ ID NO: 9:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 9:

GGGAGGACGA UGCGGGGGCC GGAUUUGAAC CGACGACUUC GGGUUAUGAG     50

CCCGACGUCA GACGACUCGC CCGA     74

( 2 ) INFORMATION FOR SEQ ID NO: 10:

( i ) SEQUENCE CHARACTERISTICS:

(A) LENGTH: 71 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 10:

```
GGGAGGACGA UGCGGUCCAG GGAUUGAAGU GUCGGGGUAG GAACAUAAAG            50
GCGGCCAGAC GACUCGCCCG A                                          71
```

(2) INFORMATION FOR SEQ ID NO: 11:

(i) SEQUENCE CHARACTERISTICS:
(A) LENGTH: 70 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 11:

```
GGGAGGACGA UGCGGAAGUU CUAACAAGUU AGUGGAAGGU UCCACUUGAA            50
UGUACAGACG ACUCGCCCGA                                            70
```

(2) INFORMATION FOR SEQ ID NO: 12:

(i) SEQUENCE CHARACTERISTICS:
(A) LENGTH: 44 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 12:

```
GGGAGGACGA UGCGGAUGGA GCUGAAAUCA GACGACUCGC CCGA                 44
```

(2) INFORMATION FOR SEQ ID NO: 13:

(i) SEQUENCE CHARACTERISTICS:
(A) LENGTH: 71 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 13:

```
GGGAGGACGA UGCGGGUGGG AAGAUGAGCC GGUCGGCAGU AAUGUGACAC            50
UGCGGCAGAC GACUCGCCCG A                                          71
```

(2) INFORMATION FOR SEQ ID NO: 14:

(i) SEQUENCE CHARACTERISTICS:
(A) LENGTH: 70 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 14:

```
GGGAGGACGA UGCGGGAGGG AAUGAGGAAA CAACUAGCAG AUAACCGAGC            50
UGGCCAGACG ACUCGCCCGA                                            70
```

( 2 ) INFORMATION FOR SEQ ID NO: 15:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 15:

GGGAGGACGA UGCGGAUGGA GCUGAAAUCA GACGACUCGC CCGA     44

( 2 ) INFORMATION FOR SEQ ID NO: 16:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 16:

GGGAGGACGA UGCGGUUGCU CUACAAUGAC GCGGUGACUC CGCAGUUCUU     50

GGACACAGAC GACUCGCCCG A     71

( 2 ) INFORMATION FOR SEQ ID NO: 17:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 17:

GGGAGGACGA UGCGGGAGGG GAGAAGAAUG CAGGAAACAG CGAAAUGCGU     50

GUGGCCAGAC GACUCGCCCG A     71

( 2 ) INFORMATION FOR SEQ ID NO: 18:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 18:

GGGAGGACGA UGCGGGCGGG AAGAGCUAAU GGAAGUGGAA UCAGUCACAG     50

UGCGGCAGAC GACUCGCCCG A     71

( 2 ) INFORMATION FOR SEQ ID NO: 19:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 19:

GGGAGGACGA UGCGGGCUUA GGGAAAUGGU UCUGAGGUGG UCAGACGACU     50

CGCCCGA 57

( 2 ) INFORMATION FOR SEQ ID NO: 20:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 20:

GGGAGGACGA UGCGGGAAGG GAACAGGAUA AGACAAGUCG AACAAAGCCG 50

AGGUGCAGAC GACUCGCCCG A 71

( 2 ) INFORMATION FOR SEQ ID NO: 21:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 21:

GGGAGGACGA UGCGGAUGGA GCUGAAAUCA GACGACUCGC CCGA 44

( 2 ) INFORMATION FOR SEQ ID NO: 22:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 22:

GGGAGGACGA UGCGGGGAGA CGUAGACGGG AACAUAGAAC GAACAUCAAC 50

GCGGCCAGAC GACUCGCCCG A 71

( 2 ) INFORMATION FOR SEQ ID NO: 23:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:23:

GGGAGGACGA UGCGGGAAGU GGAUAGAACA GUCAGAAAUG UAAGCGUGAG 50

GUGCAGACGA CUCGCCCGA 69

( 2 ) INFORMATION FOR SEQ ID NO: 24:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 24:

GGGAGGACGA UGCGGGAAGG GUAGGAAGGU CAAGAGGAAA CAGCGCUUCG    50

GGGUGCAGAC GACUCGCCCG A    71

( 2 ) INFORMATION FOR SEQ ID NO: 25:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 25:

GGGAGGACGA UGCGGGGCAA AGGAAGUUGG AAUCGGGACU AAGUAGUGUG    50

UGGCCAGACG ACUCGCCCGA    70

( 2 ) INFORMATION FOR SEQ ID NO: 26:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 26:

GGGAGGACGA UGCGGAGAAC CAACAGAGCC CCCUGGUGGU GGGGGAAGGA    50

UUCUCAGACG ACUCGCCCGA    70

( 2 ) INFORMATION FOR SEQ ID NO: 27:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 27:

GGGAGGACGA UGCGGACACA CAAGUGAAGG UCAGACGCGA AUUACGUGGG    50

UGGGCAGACG ACUCGCCCGA    70

( 2 ) INFORMATION FOR SEQ ID NO: 28:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 28:

GGGAGGACGA UGCGGUCGUG GGGUGGGUGG GGGCAGCGUU GGAAUAAGUA    50

ACUGGUAACG GCUGGCCAGA CGACUCGCCC GA    82

( 2 ) INFORMATION FOR SEQ ID NO: 29:

( i ) SEQUENCE CHARACTERISTICS:
        ( A ) LENGTH: 71 base pairs
        ( B ) TYPE: nucleic acid
        ( C ) STRANDEDNESS: single ( D ) TOPOLOGY: linear ( i i ) MOLECULE TYPE: RNA ( x i ) SEQUENCE DESCRIPTION: SEQ ID NO: 29:

GGGAGGACGA UGCGGGGUGG GUGGUUACCU GUAAUUAUAU UGAUUCUGGC 50

UUUAGCAGAC GACUCGCCCG A 71

( 2 ) INFORMATION FOR SEQ ID NO: 30:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 30:

GGGAGGACGA UGCGGCCCCU UAGCUCAGUG GUUAGAGCAG ACGACUCGCC 50

CGA 53

( 2 ) INFORMATION FOR SEQ ID NO: 31:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 31:

GGGAGGACGA UGCGGUAACG UGGAAUAGGG UUAAACAGCU GGAAAUAACG 50

UAGGUGGCCA GACGACUCGC CCGA 74

( 2 ) INFORMATION FOR SEQ ID NO: 32:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 32:

GGGAGGACGA UGCGGGUAGG GAGUAGGACA GACAUAACAG UGCAACCAUC 50

GUGGCCAGAC GACUCGCCCG A 71

( 2 ) INFORMATION FOR SEQ ID NO: 33:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 33:

GGGAGGACGA UGCGGAAACG GCGUGGCAAA AGUGAGGGGG UAGGAUGUAC 50

CAUGGGUCAG ACGACUCGCC CGA 73

( 2 ) INFORMATION FOR SEQ ID NO: 34:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 34:

GGGAGGACGA UGCGGGAGGG GAAAAUGAGA CCGACAGAUU GACGGAAGUA    50

CUGGGCAGAC GACUCGCCCG A    71

( 2 ) INFORMATION FOR SEQ ID NO: 35:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 35:

GGGAGGACGA UGCGGGCAUU CGUCAAUACC UUGUUUUAUU CCUUUUCUAG    50

CGGCCCAGAC GACUCGCCCG A    71

( 2 ) INFORMATION FOR SEQ ID NO: 36:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 36:

GGGAGGACGA UGCGGAUCGU AAUCGCCACU ACUACUUUCC GAACCCGCAC    50

GUGGCCAGAC GACUCGCCCG A    71

( 2 ) INFORMATION FOR SEQ ID NO: 37:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 37:

GGGAGGACGA UGCGGCGUCC CGAGUCACGC UGUCCUGAUA ACCUUCUCUG    50

UGCCCAGACG ACUCGCCCGA    70

( 2 ) INFORMATION FOR SEQ ID NO:38:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 38:

GGGAGGACGA UGCGGGAUCC UUUGUGGGCU CUUGUUGACC CCCUCGUUGU    50

CCCCCCCAGA CGACUCGCCC GA 72

( 2 ) INFORMATION FOR SEQ ID NO: 39:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 39:

GGGAGGACGA UGCGGCGGGU ACUCUUCGCC AGCUCCUCCA AGCGCGACCU 50

GUGCCCAGAC GACUCGCCCG A 71

( 2 ) INFORMATION FOR SEQ ID NO: 40:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 40:

GGGAGGACGA UGCGGUUUCG AAUAGGGCCA UUUCUCACUA GCUAUCCUAC 50

CCUGCCCAGA CGACUCGCCC GA 72

( 2 ) INFORMATION FOR SEQ ID NO: 41:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 41:

GGGAGGACGA UGCGGAUAAU GGCUAGAACU AGCUCGCAUC UUGGUGUCCG 50

GUGCCCAGAC GACUCGCCCG A 71

( 2 ) INFORMATION FOR SEQ ID NO: 42:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 42:

GGGAGGACGA UGCGGGACCA GAUGGCGGAU UUUUCAGCAA UCCUCCCCG 50

CUGCCCAGAC GACUCGCCCG A 71

( 2 ) INFORMATION FOR SEQ ID NO: 43:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear (i i) MOLECULE TYPE: RNA (x i) SEQUENCE DESCRIPTION: SEQ ID NO: 43:

| GGGAGGACGA | UGCGGUGAUG | GCGACCAGUC | AAACCGGUGC | UUUUACUCCC | 50 |
| CCGCCAGACG | ACUCGCCCGA | | | | 70 |

(2) INFORMATION FOR SEQ ID NO: 44:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO: 44:

| GGGAGGACGA | UGCGGGAAUU | AACAGGGCCA | GAAUUCUCAU | CUNNCUUCCC | 50 |
| GUGACCCAGA | CGACUCGCCC | GA | | | 72 |

(2) INFORMATION FOR SEQ ID NO: 45:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO: 45:

| GGGAGGACGA | UGCGGCACCU | UAGACCUGUC | CUCCAAGCGU | GAGUUGCUGU | 50 |
| GGCCCAGACG | ACUCGCCCGA | | | | 70 |

(2) INFORMATION FOR SEQ ID NO: 46:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO: 46:

| GGGAGGACGA | UGCGGUGGUC | UCCCAAUUCU | AAACUUUCUC | CAUCGUAUCU | 50 |
| GGGCCAGACG | ACUCGCCCGA | | | | 70 |

(2) INFORMATION FOR SEQ ID NO: 47:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO:47:

| GGGAGGACGA | UGCGGUCAUG | GUGUCUUUCC | ACAGCUCUUC | CCAUGAUCGC | 50 |
| CCGGCCAGAC | GACUCGCCCG | A | | | 71 |

(2) INFORMATION FOR SEQ ID NO: 48:

(i) SEQUENCE CHARACTERISTICS:

( A ) LENGTH: 71 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 48:

GGGAGGACGA UGCGGGAAUU CCCAGCGCUU GACUGAUACA AACNUUCCCG        50

UGCCCCAGAC GACUCGCCCG A        71

( 2 ) INFORMATION FOR SEQ ID NO:49:

( i ) SEQUENCE CHARACTERISTICS:
( A ) LENGTH: 70 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 49:

GGGAGGACGA UGCGGCAANN NNNNCUCUC UCCUGGCGUU CCGCAACCCG        50

CCCCCAGACG ACUCGCCCGA        70

( 2 ) INFORMATION FOR SEQ ID NO: 50:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 50:

GGGAGGACGA UGCGGAGUAU UCCAGCCUGG AUUCAUAGUC AGUGCUCUCC        50

GUGCCCAGAC GACUCGCCCG A        71

( 2 ) INFORMATION FOR SEQ ID NO: 51:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 51:

GGGAGGACGA UGCGGUCCUA GCAGCGAUUC AUCCCGUUC UCUCAGCGUU        50

GCCCCCAGAC GACUCGCCCG A        71

( 2 ) INFORMATION FOR SEQ ID NO: 52:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:52:

GGGAGGACGA UGCGGCCUGA AGUACAGGCU CUAAACUCCA AGCGCGACCG        50

UCCGCCAGAC GACUCGCCCG A        71

( 2 ) INFORMATION FOR SEQ ID NO: 53:

( i ) SEQUENCE CHARACTERISTICS:
    ( A ) LENGTH: 68 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 53:

GGGAGGACGA UGCGGCCCUA CCACUUUUUC CCUCUACUGU UAUCCUGUCC        50

CCCAGACGAC UCGCCCGA        68

( 2 ) INFORMATION FOR SEQ ID NO: 54:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 54:

GGGAGGACGA UGCGGUGGUC UCCCUAGAUC UACAGCACUU CCAUCGCAUU        50

GGGCCAGACG ACUCGCCCGA        70

( 2 ) INFORMATION FOR SEQ ID NO: 55:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 55:

GGGAGGACGA UGCGGUCAAG CUUAACAGUC UGGCAAUGGC CAUUAUGGCG        50

CCCCAGACGA CUCGCCCGA        69

( 2 ) INFORMATION FOR SEQ ID NO: 56:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 56:

GGGAGGACGA UGCGGCAGUC UGGAUCUCUA UUGGAAUUUA GUCCUCAACU        50

GUGCCCCAGA CGACUCGCCC GA        72

( 2 ) INFORMATION FOR SEQ ID NO: 57:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 57:

GGGAGGACGA UGCGGGAUUC UUUCGGCAAG UGAAAAAUAU CCUUGCUUCC 50

CGAGCCAGAC GACUCGCCCG A 71

( 2 ) INFORMATION FOR SEQ ID NO: 58:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 58:

GGGAGGACGA UGCGGGGACU UCAACUAAGU CCUCAUUUGC CUCGCUCCUC 50

GUGCCCAGAC GACUCGCCCG A 71

( 2 ) INFORMATION FOR SEQ ID NO: 59:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 59:

GGGAGGACGA UGCGGAACGG AGAUGUCCCC UCAAMAUUUA CCGUCUCCGU 50

UUGCGCCCCA GACGACUCGC CCGA 74

( 2 ) INFORMATION FOR SEQ ID NO: 60:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:60:

GGGAGGACGA UGCGGCGAAA UUAGCUUCUU AUGACUCACG UUUCCUUGCC 50

GCCCCAGACG ACUCGCCCGA 70

( 2 ) INFORMATION FOR SEQ ID NO: 61:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 61:

GGGAGGACGA UGCGGGCCCG AUCUACUGCA UUACCGAAAC GAUUCCCCA 50

CUGUGCAGAC GACUCGCCCG A 71

( 2 ) INFORMATION FOR SEQ ID NO: 62:

( i ) SEQUENCE CHARACTERISTICS:
        ( A ) LENGTH: 71 base pairs
        ( B ) TYPE: nucleic acid (C) STRANDEDNESS: single
(D) TOPOLOGY: linear (i i) MOLECULE TYPE: RNA (x i) SEQUENCE DESCRIPTION: SEQ ID NO: 62:

GGGAGGACGA UGCGGNGACU GAUUUUUCCU UGNCAGUGUA AUUUCCUGGC  50

UGCCCCAGAC GACUCGCCCG A  71

(2) INFORMATION FOR SEQ ID NO: 63:

(i) SEQUENCE CHARACTERISTICS:
(A) LENGTH: 71 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 63:

GGGAGGACGA UGCGGGGACU UUGACAGGCA UUGAUUUCGA CCUGUUCCCC  50

GUGGCCAGAC GACUCGCCCG A  71

(2) INFORMATION FOR SEQ ID NO: 64:

(i) SEQUENCE CHARACTERISTICS:
(A) LENGTH: 71 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 64:

GGGAGGACGA UGCGGCGACA CAAUAGCCUU UGAUCCCAUG AUGGCUCGCC  50

GUGCCCAGAC GACUCGCCCG A  71

(2) INFORMATION FOR SEQ ID NO: 65:

(i) SEQUENCE CHARACTERISTICS:
(A) LENGTH: 71 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 65:

GGGAGGACGA UGCGGUGUAG UUUCCCUGUA UGCCAUUCUU UCCCAUGCCG  50

CACGCCAGAC GACUCGCCCG A  71

(2) INFORMATION FOR SEQ ID NO: 66:

(i) SEQUENCE CHARACTERISTICS:
(A) LENGTH: 71 base pairs
(B) TYPE: nucleic acid
(C) STRANDEDNESS: single
(D) TOPOLOGY: linear (i i) MOLECULE TYPE: RNA (x i) SEQUENCE DESCRIPTION: SEQ ID NO: 66:

GGGAGGACGA UGCGGUCGAG UGUUCUCCUU CGGUAACUAU UNNNNAUUUC  50

GUGCCCAGAC GACUCGCCCG A  71

( 2 ) INFORMATION FOR SEQ ID NO: 67:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 67:

```
GGGAGGACGA  UGCGGGUCGU  AUUCAUCUCC  UUGUUCUGUU  UCGUUGCACC        50
UGGCCCAGAC  GACUCGCCCG  A                                         71
```

( 2 ) INFORMATION FOR SEQ ID NO: 68:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 68:

```
GGGAGGACGA  UGCGGGGACU  UUGACAGGCA  UUGAUUUCGA  CGUGUUCCCC        50
GUGGCCAGAC  GACUCGCCCG  A                                         71
```

( 2 ) INFORMATION FOR SEQ ID NO: 69:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 69:

```
GGGAGGACGA  UGCGGUGAUC  AAUCGGCGCU  UUACUCUUGC  GCUCACCGUG        50
CCCCAGACGA  CUCGCCCGA                                             69
```

( 2 ) INFORMATION FOR SEQ ID NO: 70:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 70:

```
GGGAGGACGA  UGCGGCAGUC  UCCCUAGGUU  UCAUCUCUGC  AGCAUUCCGG        50
GGUNCCAGAC  GACUCGCCCG  A                                         71
```

( 2 ) INFORMATION FOR SEQ ID NO: 71:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 71:

GGGAGGACGA UGCGGAUCAA AAGCACUCAU UCCCGUGCUC GCUUCAUUGG 50

UCCCCCAGAC GACUCGCCCG A 71

(2) INFORMATION FOR SEQ ID NO: 72:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 72:

GGGAGGACGA UGCGGAAGAU CUCCCAACUG CUGUGGCUAA UAAUUCUCUC 50

CGCGUCCCCA GACGACUCGC CCGA 74

(2) INFORMATION FOR SEQ ID NO: 73:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 73:

GGGAGGACGA UGCGGUCCGU CAUAACGGCC AUAAACUGCG AAUACUCCCU 50

GGCCCAGACG ACUCGCCCGA 70

(2) INFORMATION FOR SEQ ID NO: 74:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 74:

GGGAGGACGA UGCGGGGACA AWYAGCGGUG UCUUUUCAUU UNKAUCCUCC 50

GACRUCCCAG ACGACUCGCC CGA 73

(2) INFORMATION FOR SEQ ID NO: 75:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 75:

GGGAGGACGA UGCGGUGACU AUCUGGCUCG AUCCAAUCAC CCGAGCCCAC 50

CGCGCCAGAC GACUCGCCCG A 71

(2) INFORMATION FOR SEQ ID NO: 76:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO: 76:

| GGGAGGACGA | UGCGGGAACU | AAUGGCCGUG | AUUAACCAAU | GCAGGCUUCC | 50 |
| UGCGCCAGAC | GACUCGCCCG | A | | | 71 |

(2) INFORMATION FOR SEQ ID NO: 77:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (i i) MOLECULE TYPE: RNA (x i) SEQUENCE DESCRIPTION: SEQ ID NO: 77:

| GGGAGGACGA | UGCGGUGACA | UGGAAUUUUC | UACGGGCCCG | AUCCUGCCAG | 50 |
| CCGUGUGCAG | ACGACUCGCC | CGA | | | 73 |

HIGH AFFINITY HKGF NUCLEIC ACID LIGANDS AND INHIBITORS

RELATED APPLICATIONS

This application is a Continuation-in-Part of U.S. patent application Ser. No. 07/714,131, filed Jun. 10, 1991, entitled Nucleic Acid Ligands now issued as U.S. Pat. No. 5,475,096, U.S. patent application Ser. No. 07/931,473, filed Aug. 17, 1992, entitled Nucleic Acid Ligands, now issued as U.S. Pat. No. 5,270,163, U.S. patent application Ser. No. 07/964,624, filed Oct. 21, 1992, entitled Methods of Producing Nucleic Acid Ligands now issued as U.S. Pat. No. 5,496,938, and U.S. patent application Ser. No. 08/117,991, filed Sep. 8, 1993, entitled High-Affinity Nucleic Acid Ligands Containing Modified Nucleotides now abandoned, U.S. patent application Ser. No. 07/714,131 is a Continuation-in-Part of U.S. patent application Ser. No. 07/536,428, filed Jun. 11, 1990, entitled Systematic Evolution of Ligands by EXponential Enrichment, now abandoned.

FIELD OF THE INVENTION

Described herein are methods for identifying and preparing high-affinity nucleic acid ligands to hKGF. The method utilized herein for identifying such nucleic acid ligands is called SELEX, an acronym for Systematic Evolution of Ligands by EXponential enrichment. This invention includes high affinity nucleic acid ligands of hKGF. Further disclosed are RNA ligands to hKGF. Also included are oligonucleotides containing nucleotide derivatives chemically modified at the 2'-positions of pyrimidines. Additionally disclosed are RNA ligands to hKGF containing 2'—$NH_2$-modifications or 2'—F-modifications. This invention also includes high affinity nucleic acid inhibitors of hKGF. The oligonucleotides of the present invention are useful as pharmaceuticals or diagnostic agents.

BACKGROUND OF THE INVENTION a) Biochemical properties of hKGF

Human Keratinocyte Growth Factor (hKGF) is a small (26–28KD) basic heparin-binding growth factor and a member of the FGF family. hKGF is a relatively newly identified molecule which is also known as FGF-7 (Finch et al., 1989, Science 244: 752–755). It is a growth factor specific for epithelial cells (Rubin et al., 1989, Proc Natl Acad Sci USA 86: 802–806), and its main function is in development/morphogenesis (Werner et al., 1994, Science 266: 819–822) and in wound healing (Werner et al., 1992, Proc Natl Acad Sci USA 89: 6896–6900). The major in vivo source of hKGF is stromal fibroblasts (Finch et al., 1989, Science 244: 752–755). Microvascular endothelial cells (Smola et al., 1993, J Cell Biol 122: 417–429) and very recently, activated intraepithelial gd T cells (Boismenu et al., 1994, Science 266: 1253–1255) have also been shown to synthesize hKGF. hKGF expression is stimulated in wounds (Werner et al., 1992, Proc Natl Acad Sci USA 89: 6896–6900). Several cytokines are shown to be hKGF inducers (Brauchle et al., 1994, Oncogene 9: 3199–3204), with IL-1 the most potent one (Brauchle et al., 1994, Oncogene 9: 3199–3204; Chedid et al., 1994, J Biol Chem 269: 10753–10757). Unlike bFGF, hKGF has a signal peptide and thus is secreted by producing cells (Finch et al., 1989, Science 244: 752–755). hKGF can be overexpressed in E. coli and the recombinant protein (~19–21 KD) is biologically active (Ron et al., 1993, J Biol Chem 268: 2984–2988). The E. coli derived recombinant protein is 10 times more mitogenic than the native protein (Ron et al., 1993, J Biol Chem 268: 2984–2988). This difference may be due to glycosylation. The native protein has a potential Asn glycosylation site (Ron et al., 1993, J Biol Chem 268: 2984–2988).

The hKGF bioactivity is mediated through a specific cell surface receptor (Miki et al., 1991, Science 251: 72–75). The hKGF receptor is a modified FGF receptor resulting from alternative splicing of the C-terminal extracellular region of the FGF-R2 (Miki et al., 1992, Proc Natl Acad Sci USA 89: 246–250). NIH/3T3 cells transfected with the hKGF receptor express high affinity (~200 pM) binding sites for hKGF (Miki et al., 1992, Proc Natl Acad Sci USA 89: 246–250). The approximate number of specific binding sites per NIH/3T3 cell is about 500,000 (D. Bottaro and S. Aaronson, personal communication). The hKGF receptor binds hKGF and aFGF with similar affinities, and bFGF with about 20 fold less affinity (Miki et al., 1991, Science 251: 72–75; Miki et al., 1992, Proc Natl Acad Sci USA 89: 246–250). A variant of the hKGF receptor has been found to be an amplified gene (i.e., one gene, multiple copies), designated K-SAM, in a human stomach carcinoma cell line (Hattori et al., 1990, Proc natl Acad Sci USA 87: 5983–5987).

Heparin has been reported to be an inhibitor of hKGF bioactivity (Ron et al., 1993, J Biol Chem 268: 2984–2988). This is in contrast to the agonistic effect of heparin for aFGF (Spivak-Kroixman et al., 1994, Cell 79: 1015–1024).

b) Role of hKGF in human disease

The recombinant hKGF molecule has been available since 1993. Therefore, there is limited information on the role of hKGF in human disease. The published literature, however, contains evidence that strongly suggests a role for hKGF in at least two human diseases, namely psoriasis and cancer. hKGF has also been implicated in inflammatory bowel disease (P. Finch, personal communication).

Psoriasis

Psoriasis is a skin disorder which can be debilitating (Greaves et al., 1995, N Eng J Medicine 332: 581–588), characterized by hyperproliferation of the epidermis and incomplete differentiation of keratinocytes, together with dermal inflammation (Abel et al., 1994, Scientific American Medicine III-1 to III-18; Greaves et al., 1995, N Eng J Medicine 332: 581–588). There is not yet an effective treatment for psoriasis (Anonymous, 1993, Drug & Market Development 4: 89–101; Abel et al., 1994, Scientific American Medicine III-1 to III-18; Greaves et al., 1995, N Eng J Medicine 332: 581–588). Psoriasis occurs in 0.5 to 2.8 percent of the population with the highest incidence in Scandinavia. In the US in 1992, it was estimated that 4–8 million people affected with psoriasis spent about $600 million for various drugs and related therapies, none of which is very effective. Most of the expenditure was made by about 400,000 patients with severe psoriasis spending $1,000–1,500 annually on treatment. There are about 200,000 new cases of psoriasis every year.

The basic cause of the disorder is not known, but it results from a primary or secondary defect in the mechanisms that regulate epidermal keratinocyte cell division (Abel et al., 1994, Scientific American Medicine III-1 to III-18). Psoriasis responds to steroids and cyclosporine and in that sense is characterized as an immune disease (Abel et al., 1994, Scientific American Medicine III-1 to III-18). Since hKGF is the primary specific growth factor for keratinocytes, its overexpression and deregulation are primary candidates as the cause of keratinocyte hyperproliferation in psoriasis. The demonstration that the immune system is a prime regulator of hKGF release (Boismenu et al., 1994, Science 266: 1253–1255; Brauchle et al., 1994, Oncogene 9: 3199–3204; Chedid et al., 1994, J Biol Chem 269: 10753–10757)

strengthens the notion that hKGF deregulation is the cause of psoriasis. Furthermore, application of hKGF in porcine wounds creates a histological appearance resembling psoriasis (Staiano-Coico et al., 1993, *J Ex Med* 178: 865–878); keratinocyte derived hKGF in transgenic mice causes pathology reminiscent to psoriasis (Guo et al., 1993, *EMBO J* 12: 973–986); in situ hybridization experiments demonstrated a moderate and a strong upregulation of hKGF and hKGF receptors respectively in psoriasis (P. Finch, personal communication). In situ hybridization experiments also demonstrated involvement of hKGF in another immune disease namely, inflammatory bowel disease (P. Finch, personal communication).

Cancer

It is well established in the literature that deregulation of the expression of growth factors and growth factor recept hKGF and/or its receptor is expected to be the transformation event in some human cancers. The transforming ability of the hKGF system has been demonstrated in vitro (Miki et al., 1991, *Science* 251: 72–75). In another study, carcinoma cell-lines have been found to express the hKGF receptor and to respond to hKGF but not to aFGF, while sarcoma cell-lines do not express hKGF receptors and respond to aFGF but not to hKGF (Ishii et al., 1994, *Cancer Res* 54: 518–522).

Gastrointestinal Cancer

Several poorly differentiated stomach cancers have an amplified gene, designated K-sam, which is an isoform of the hKGF-receptor (Katoh et al., 1992, *Proc Natl Acad Sci USA* 89: 2960–2964). In vivo administration of hKGF to rats causes proliferation of pancreatic ductal epithelial cell (Yi et al., 1994, *Am J Pathol* 145: 80–85), hepatocytes, and epithelial cells throughout the gastrointestinal tract (Housley et al., 1994, *J Clin Invest* 94: 1764–1777).

Lung Cancer

Administration of hKGF to rats causes type II pneumocyte hyperplasia similar to the bronchoalveolar cell variant of lung carcinoma (Ulich et al., 1994, *J Clin Invest* 93: 1298–1306).

Breast Cancer

In vivo hKGF causes mammary duct dilation and rampant epithelial hyperplasia, both of which are common features of breast cancers (Ulich et al., 1994, *Am J Pathol* 144: 862–868; Yi et al., 1994, *Am J Pathol* 145: 1015–1022). However, the ductal epithelium of breastfeeding rats is resistant to the growth promoting effects of hKGF and this is of interest in regard to epidemiological observations that pregnancy in women decreases susceptibility to breast cancer and that dairy cows almost never develop breast cancer (Kuzma, 1977, *Breast in Pathology*, Mosby Co.). There is additional supporting evidence implicating hKGF in breast cancer. hKGF mRNA has been detected recently in normal human breast tissue and in 12 of 15 breast tumor samples tested (Koos et al., 1993, *J Steroid Biochem Molec Biol* 45: 217–225). The presence of hKGF mRNA in breast tumors considered in conjunction with the observation that hKGF is present in nonneoplastic mammary glands and that hKGF causes rampant proliferation of mammary epithelium suggests that hKGF may be an autocrine or paracrine growth factor important in the regulation of the growth of normal and neoplastic mammary epithelium (Ulich et al., 1994, *Am J Pathol* 144: 862–868). Infiltrating ductal mammary adenocarcinoma is characteristically enveloped by a desmoplastic stroma that has been postulated to represent a defensive host response to the carcinoma (Ulich et al., 1994, *Am J Pathol* 144: 862–868). Since hKGF is stroma derived it is possible that the desmoplasmic stroma contributes rather than inhibits the growth of the tumor.

Prostate Cancer

The growth promoting effect of androgens on prostate tumors appears to be mediated through hKGF (Yan et al., 1992, *Mol Endo* 6: 2123–2128), as androgens induce the expression of hKGF in prostate stroma cells. Prostate tumors that are androgen dependent in vivo, are androgen independent in vitro, but hKGF dependent (Yan et al., 1992, *Mol Endo* 6: 2123–2128). In agreement with the role of hKGF as andromedin is the observation that hKGF functions in epithelial induction during seminal vesicle development, a process that is directed by androgen (Alarid et al., 1994, *Proc Natl Acad Sci USA* 91: 1074–1078). Furthermore, hKGF causes aberrant activation of the androgen receptor, thus probably contributing to the failure of androgen ablation therapy in prostate cancer (Culig et al., 1994, *Cancer Res* 54: 5474–5478). Based on this information, it is possible that genetic alterations cause hKGF to escape androgen regulation and thus convert the androgen dependent tumor into an androgen independent, highly malignant tumor. Such tumors would still be able to express the androgen regulated marker PSA, as hKGF also causes the aberrant activation of the androgen receptor. It is also likely that hKGF might be responsible for Benign Prostate Hypertrophy (BPH), a common health problem in older men (D. Bottaro, personal communication).

d) hKGF Competitors

To date, a monoclonal antibody and a short hKGF-receptor derived peptide (25-mer) have been described as hKGF competitors (Bottaro et al., 1993, *J Biol Chem* 268: 9180–9183). The monoclonal antibody, designated 1G4, has a Kd of 200 pM for hKGF. The short peptide inhibits hKGF binding to the cell surface of NIH/3T3 cells expressing the human receptor with a Ki of about 1–5 $\mu$M. Bottaro et al. (WO 94/25057) provide hKGF-receptor peptides which inhibit binding between hKGF and its receptor. Also provided is a method of assaying test compounds for the ability to inhibit hKGF receptor-mediated cell proliferation.

e) Assaying for receptor-growth factor interaction

Blocking the interaction of growth factors and lymphokines with their cell surface receptor using antagonists has been an approach for disease treatment. The discovery of such antagonists requires the availability of biochemical assays for the receptor-growth factor or lymphokine interaction. A classic assay has been the competitive inhibition of radiolabeled growth factor or lymphokine (tracer) to its cell surface receptor. These types of assays utilize cell lines that express the relevant receptor on their surface and determines the amount of cell bound tracer in the presence of various concentrations of potential antagonists. Additionally, other assays utilize membrane extracts from cell lines that express the relevant receptor, and tracer binding is followed by filter binding (see Nenquest Drug Discovery System: Human Tumor Necrosis Factor-Alpha, NEN Research Products, E. I. DePont de Nemours & Co. (Inc.), Boston, Mass.) or by immobilizing the membrane extracts onto solid supports (Urdal et al., 1988, *J Biol Chem* 263: 2870–2877; Smith et al., 1991, *Bioch Bioph Res Comm* 176: 335–342). Receptor induced electrophoretic mobility shift of tracer has been applied to identify the presence and size of cell surface receptors by crosslinking the receptor to the tracer and then analyzing on denaturing gels (for example see Kull et al., 1985, *Proc nati Acad Sci USA* 82: 5756–5760; Hohmann et al., 1989, *J Biol Chem* 264: 14927–14934; Stauber et al., 1989, *J Biol Chem* 264: 3573–3576). The use of native gels and non-crosslinked complexes has not been described for growth factors or lymphokines and their receptors, but has been widely applied to study nucleic acid protein interactions (Sambrook et al., 1989, *Molecular Cloning: A Laboratory Manual*, Cold Spring Harbor Laboratory, Cold Spring Harbor, N.Y.).

Screening of various cancer cell lines for the presence of hKGF receptors by PCR, revealed that all carcinoma cell lines express hKGF receptor mRNA while sarcoma cell lines do not. The presence of MRNA does not necessarily mean that hKGF receptor will be present on the surface of these cells. For hKGF, only cell based assays have been described using Balb/MK keratinocytes (Weissman, (1983) *Cell* 32: 599–606) or NIH/3T3 cells transfected with the hKGF receptor (Miki, (1992) *Proc. Natl. Acad. Sci. USA* 89:246–250).

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands now issued as U.S. Pat. No. 5,475,096, U.S. patent application Ser. No. 07/931,473, filed Aug. 17, 1992, entitled Nucleic Acid Ligands, now U.S. Pat. No. 5,270,163 (see also WO 91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX." U.S. patent application Ser. No. 08/143,564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled High Affinity Nucleic Acid Ligands Containing Modified Nucleotides, that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'—$NH_2$), 2'-fluoro (2'—F), and/or 2'-O-methyl (2'—OMe). Each of these applications is specifically incorporated herein by reference.

BRIEF SUMMARY OF THE INVENTION

The present invention includes methods of identifying and producing nucleic acid ligands to human keratinocyte growth factor (hKGF), and homologous KGF proteins, and the nucleic acid ligands so identified and produced. In particular, RNA sequences are provided that are capable of binding specifically to hKGF. Specifically included in the invention are the RNA ligand sequences shown in Table 3 (SEQ ID NOS.: 4–77). These RNA ligand sequences include 2'—$NH_2$ and 2'—F modified pyrimidines.

Also included in this invention are RNA ligands of hKGF that inhibit the function of hKGF, presumably by inhibition of the interaction of hKGF with its receptor.

Further included in this invention is a method of identifying nucleic acid ligands and nucleic acid ligand sequences to hKGF comprising the steps of (a) preparing a candidate mixture of nucleic acids, (b) contacting the candidate mixture of nucleic acids with hKGF, (c) partitioning between members of said candidate mixture on the basis of affinity to hKGF, and (d) amplifying the selected molecules to yield a mixture of nucleic acids enriched for nucleic acid sequences with a relatively higher affinity for binding to hKGF.

More specifically, the present invention includes the RNA ligands to hKGF identified according to the above-described method, including those ligands shown in Table 3 (SEQ ID NOS: 4–77). Also included are RNA ligands to hKGF that are substantially homologous to any of the given ligands and that have substantially the same ability to bind hKGF and inhibit the interaction of hKGF with its receptor. Further included in this invention are nucleic acid ligands to hKGF that have substantially the same structural form as the ligands presented herein and that have substantially the same ability to bind hKGF and inhibit the interaction of hKGF with its receptor.

The present invention also includes other modified nucleotide sequences based on the RNA ligands identified herein and mixtures of the same.

Further included in this invention is a method of assaying a test compound for the ability to inhibit hKGF receptor-mediated cell proliferation comprising the steps of (a) contacting the test compound with a hKGF nucleic acid ligand and a keratinocyte growth factor; and (b) detecting the ability of the test compound to inhibit binding between the hKGF nucleic acid ligand and the keratinocyte growth factor.

Also included in this invention is a method of assaying a test compound for the ability to inhibit the interaction of a growth factor with its plasma membrane bound receptor comprising the steps of (a) solubilizing cells containing the plasma membrane bound receptor; (b) creating a plasma membrane extract of the cells; (c) reacting the extract with labeled growth factor alone and in the presence of the test compound thereby creating complexes; (d) analyzing the complexes by electrophoresis under native conditions; (e) visualizing the complexes by imaging; and (f) comparing the image of the extract with labeled growth factor alone to the image of the extract in the presence of the test compound to determine whether the test compound inhibited the interaction between the growth factor and its plasma membrane bound receptor.

Further included in this invention is a method for assaying cells to determine whether they express a growth factor plasma membrane bound receptor comprising the steps of (a) solubilizing the cells (b) creating a plasma membrane extract of the cells (c) reacting the plasma membrane extract with a labeled growth factor (d) analyzing the reaction between the plasma membrane extract with the labeled growth factor by electrophoresis under native conditions (e) comparing the electrophoresis of step (d) with electrophoresis of labeled growth factor; and (e) visualizing the results of the electrophoresis to determine whether a complex is formed with altered mobility relative to the mobility of a labeled growth factor alone.

DETAILED DESCRIPTION OF THE INVENTION

Figure 1A:
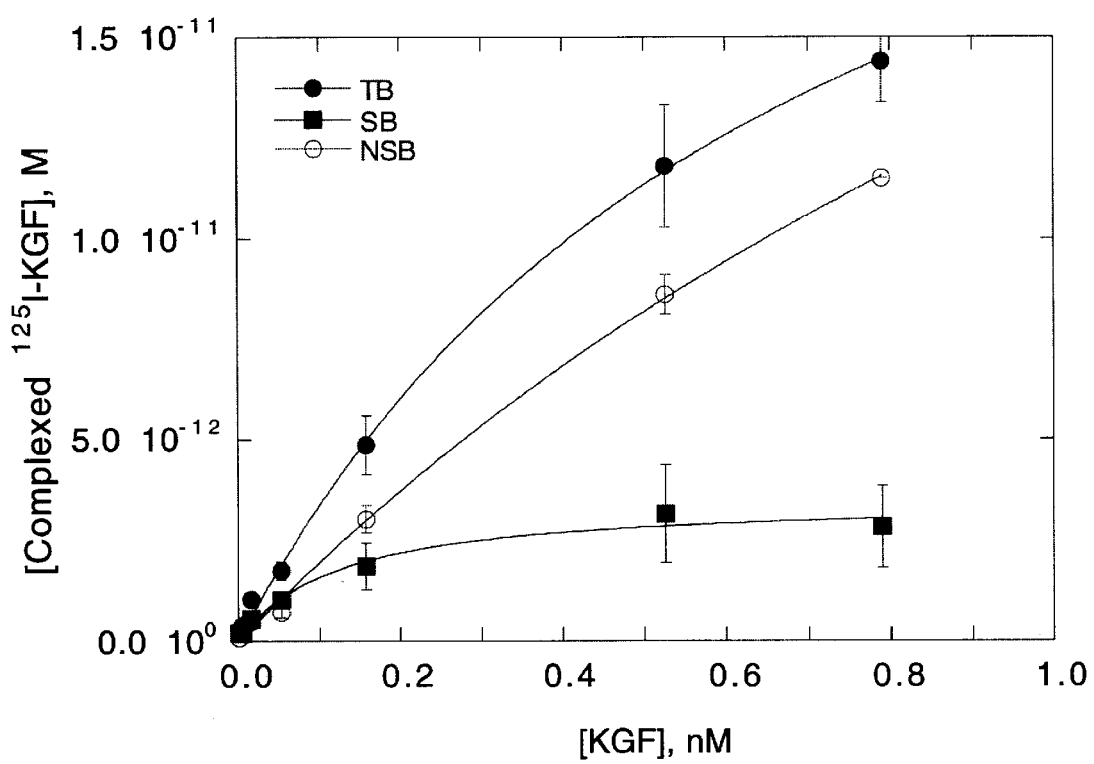
Figure 1A shows the saturation binding of radiolabeled hKGF on the surface of the PC-3 cells. TB (total binding) is the binding observed in the absence of competing unlabeled hKGF, whereas NSB (nonspecific binding) is the binding observed in the presence of 100 fold molar excess of unlabeled hKGF. SB (specific binding) demonstrates the specific binding, and this curve was derived by subtracting the NSB curve from the TB curve.

This application describes high-affinity nucleic acid ligands to hKGF identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now issued as U.S. Pat. No. 5,475,096, U.S. patent application Ser. No. 07/931,473, filed Aug. 17, 1992, entitled Nucleic Acid Ligands, now U.S. Pat. No. 5,270,163, (see also WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications.

Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to hKGF described herein may specifically be used for identification of the hKGF protein.

SELEX provides high affinity ligands of a target molecule. This represents a singular achievement that is unprecedented in the field of nucleic acids research. The present invention applies the SELEX procedure to the specific target of hKGF. In the Example section below, the experimental parameters used to isolate and identify the nucleic acid ligands to hKGF are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. The '624 application, entitled Methods of Producing Nucleic Acid Ligands now issued as U.S. Pat. No. 5,496,938, is specifically incorporated herein by reference.

In the present invention, a SELEX experiment was performed in search of RNA with specific high affinity for hKGF from degenerate libraries containing 40 random positions (40N) (Table 1). This invention includes the specific RNA ligands to hKGF shown in Table 3 (SEQ ID NOS: 4–77), identified by the methods described in Examples 1 and 2. This invention further includes RNA ligands to hKGF which inhibit the interaction of hKGF with its receptor. The scope of the ligands covered by this invention extends to all nucleic acid ligands of hKGF, modified and unmodified, identified according to the SELEX procedure. More specifically, this invention includes nucleic acid sequences that are substantially homologous to the ligands shown in Table 3 (SEQ ID NOS.: 4–77). By substantially homologous it is meant a degree of primary sequence homology in excess of 70%, most preferably in excess of 80%. A review of the sequence homologies of the ligands of hKGF shown in Table 3 (SEQ ID NOS.: 4–77) shows that sequences with little or no primary homology may have substantially the same ability to bind hKGF. For these reasons, this invention also includes nucleic acid ligands that have substantially the same structure and ability to bind hKGF as the nucleic acid ligands shown in Table 3 (SEQ ID NOS.: 4–77). Substantially the same ability to bind hKGF means that the affinity is within one or two orders of magnitude of the affinity of the ligands described herein. It is well within the skill of those of ordinary skill in the art to determine whether a given sequence—substantially homologous to those specifically described herein—has substantially the same ability to bind hKGF.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

As described above, because of their ability to selectively bind hKGF, the nucleic acid ligands to hKGF described herein are useful as pharmaceuticals. This invention, therefore, also includes a method for treating hKGF-mediated pathological conditions by administration of a nucleic acid ligand capable of binding to hKGF.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaccutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconsitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in the subsequent examples. Example 2 describes the RNA ligands to hKGF, the affinities the ligands have for hKGF, and the specificity of the RNA ligands to hKGF. Example 3 describes inhibition of hKGF binding to cell surface receptors. Example 4 reports on the inhibition of mitogenic activity of hKGF by a selected ligand.

EXAMPLE 1. EXPERIMENTAL PROCEDURES

Materials and Methods

Recombinant human Keratinocyte Growth Factor (hKGF) was purchased from Upstate Biotechnology Inc.(Lake Placid, N.Y.). $^{125}$I-labeled hKGF was prepared following a published procedure (Bottaro et al., 1990, *J Biol Chem* 265: 12767–12770). The PC-3 cells were obtained from ATCC (catalog number CRL1435). The NIH3T3 cells transfected with the hKGF receptor (NIH3T3/FGFR-2) were a generous gift from S. Aaronson and have been described elsewhere (Miki et al., 1991, *Science* 251: 72–75; Miki et al., 1992, *Proc Natl Acad Sci USA* 89: 246–250). T7 RNA polymerase, 2'—NH$_2$— and 2'—F-modified CTP and UTP were prepared at NeXstar Pharmaceuticals, Inc. (Boulder, Colo.). DNA oligonucleotides were obtained from Operon Technologies, Inc. (Alameda, Calif.). Nitrocellulose/cellulose acetate mixed matrix (HA), 0.45 $\mu$m filters were from Millipore (Bedford, Mass.). All other reagents and chemicals were from commercial sources.

SELEX

The SELEX procedure has been described in detail in U.S. Pat. No. 5,270,163 (see also Tuerk and Gold (1990) *Science* 249:505–510). A single-stranded DNA (ssDNA) pool was used to generate the double-stranded (dsDNA) template for generating the initial random sequence RNA pool by transcription. The DNA template contained 40 random nucleotides, flanked by 5' and 3' constant regions for primer anealing sites for PCR and cDNA synthesis (Table 1). The ssDNA molecules were converted to dsDNA by PCR amplification. PCR conditions were 50 mM KCl, 10 mM Tris-HCl, pH9, 0.1% Triton X-100, 3 mM MgCl$_2$, 0.5 mM of each dATP, dCTP, dGTP, and dTTP, 0.1 units/$\mu$l Taq DNA polymerase, and 2.5 nM each of 3G7 and 5G7 primers (Table 2; SEQ ID NOS. 2–3). SELEX experiments for hKGF were initiated with a random sequence pool of RNA in which all pyrimidines were 2'—NH$_2$-modified or 2'—F-modified. Transcription reactions were done with about 5 $\mu$M DNA template, 5 units/$\mu$l T7 RNA polymerase, 40 mM Tris-HCl (pH8), 12 mM MgCl$_2$, 5mM DTT, 1 mM spermidine, 0.002% Triton X-100, 4% PEG 8000, 2–4 mM each 2'OH ATP, 2'OH GTP, 2'NH2 or 2'F CTP, 2'NH$_2$ or 2'F UTP, and 0.25 $\mu$M $\alpha^{32}$P 2'OH ATP (800 Ci/mmole). To prepare binding reactions, the RNA molecules were incubated with recombinant hKGF in Dulbecco's Phosphate-Buffered Saline (DPBS) with calcium and magnesium (Life Technologies, Gaithersburg, Md., Cat. No 21300-025) containing 0.01% human serum albumin. Following incubation at room temperature (ranging from 10 minutes to 10 hours) the protein-RNA complexes were partitioned from unbound RNA by filtering through nitrocellulose. Nitrocellulose filter bound RNA was recovered by phenol/urea extraction. The partitioned RNA was reverse transcribed into cDNA by AMV reverse transcriptase at 48° C. for 60 min in 50 mM Tris-HCl pH8.3, 60 mM NaCl, 6 mM Mg(OAc)$_2$, 10 mM DTT, 50 pmol DNA 3' primer (Table 1), 0.4 mM each of dATP, dCTP, dGTP, and dTTP, and 1 unit/$\mu$l AMV RT. The cDNA was PCR amplified and used to initiate the next SELEX cycle.

Nitrocellulose Filter Partitioning

To partition the protein-RNA complexes, the binding reactions were filtered through nitrocellulose/cellulose acetated mixed matrix, 0.45 $\mu$m pore size (filter disks, Millipore, Co., Bedford, Mass.). For filtration, the filters were placed onto a vacuum manifold and wetted by aspirating 5 ml of DPBS. The binding reactions were aspirated through the filters, and following a 5 ml wash, the filters were counted in a scintillation counter (Beckmann). Higher wash volumes with DPBS or 0.5M urea were used as a means to increase selection stringency as shown in Table 2. Nitrocellulose partitioning was used for SELEX and for determining the equilibrium dissociation constants of RNA ligands to hKGF. Some RNA ligands bind monophasically while some other bind biphasically. Biphasic binding can be described as the binding of two affinity species that are not in equilibrium. Monophasic and biphasic equilibrium dissociation constants were calculated according to standard procedures.

The $K_D$s were determined by least square fitting of the data points using the software Kaleidagraph (Synergy Software, Reading, Pa.).

Cloning and Sequencing

The RNA recovered from the round 8 filters was reverse transcribed and PCR amplified. Following column purification with QIA-quick spin columns (QIAGEN, Inc., Chatsworth, Calif.) and ethanol precipitation, the amplified DNA was methylated with HpaII methylase (NEW ENGLAND BIOLABS, Beverly, Mass.). The methylated DNA was cloned into the SrfI restriction site of pCR-Script Direct SK(+) plasmid using the pCR-Script Amp SK(+) cloning kit (STRATAGENE CLONING SYSTEMS, La Jolla, Calif.). About 80 clones were sequenced with Sequenase sequencing kit (United States Biochemical Corporation, Cleveland, Ohio).

EXAMPLE 2. RNA LIGANDS TO hKGF

SELEX

To generate RNA ligands for hKGF, two parallel SELEX experiments were initiated, one with 2'—NH$_2$ and the other 2'—F pyrimidine modified RNA molecules randomized at 40 contiguous positions. The SELEX conditions and results for each round are summarized in Table 2. The starting pool contained 5×10$^{14}$ (500 pmoles) and 2.5×10$^{14}$ (250 pmoles) 2'—NH$_2$ and 2'—F pyrimidine modified RNA molecules, respectively, and bound to hKGF with an approximate $K_D$ of 30 nM. After 8 rounds of SELEX, the evolved pools bound with a $K_D$ of 0.3 nM. No further improvement in the $K_D$ was observed in the subsequent two rounds. The RNA pools from the 8th round were reverse transcribed, PCR amplified and cloned as described.

RNA sequences

In the 2'—NH$_2$ SELEX, 29 out of 31 clones were unique. In the 2'—F SELEX all 43 clones sequenced were unique. A unique sequence is defined as one that differs from all others by three or more nucleotides. Table 3 lists the sequences of all of the clones sequenced in standard single letter code (Cornish-Bowden, 1985, *Nucleic Acid Res* 13: 3021–3030). Computer assisted global and local alignment did not reveal any extensive homologies among the clones, and no obvious families were apparent. The 2'—NH$_2$ clones are in general purine rich while the 2'—F clones are pyrimidine rich. When the alignment parameters were relaxed, the Feng/Doolittle algorithm grouped the 2'—NH$_2$ clones in one family and the 2'—F clones in another. Visual inspection of the sequences suggested two and three possible families for the 2'—NH$_2$ and the 2'—F ligands, respectively.

Affinities

The dissociation constants of the hKGF ligands were determined by nitrocellulose filter binding and are listed in Table 4. Eight out of 41 2'—F ligands bound biphasically. The remaining of the 2'—F and all the 2'—NH$_2$ ligands bound monophasically. Under protein excess, biphasic binding suggests that the ligand exists as two affinity species (presumably isoconformers) that are not in equilibrium. The best 2'—F-modified ligand, K14F, binds biphasically with the high and low affinity dissociation constant at about 6 pM and 2 nM respectively. There is some observed variability in the $K_D$ determinations for the various clones and the random RNA. Despite the experimental variability in the $K_D$ determinations, the high affinity species of K14F have a 1,000–5,000 fold better affinity than the random RNA.

Among the monophasic 2'—F-modified ligands, K38F had the best $K_D$ of about 0.3 nM. The best 2'—NH$_2$-modified ligands bound with a $K_D$ of 0.4 nM which represent about 75 fold improvement over the random RNA.

Specificity of RNA Ligands to hKGF

The specificity of the K14F ligand was tested by determining its $K_D$ against rat hKGF, and the heparin binding human growth factors, aFGF, bFGF, and PDGF (Table 5). The results suggest that the K14F binds all tested targets like random RNA, except hKGF, and it can discriminate between hKGF and other similar proteins by a factor of 400–40,000.

EXAMPLE 3. INHIBITION OF hKGF BINDING TO CELL SURFACE RECEPTORS

Receptor Binding Assay

To test the ability of the hKGF ligands to competitively inhibit the binding of hKGF to its cell surface receptor, two cell lines were used. The first cell line, PC-3, is an isolate from a grade IV prostatic adenocarcinoma (ATCC CRL 1435). The second cell line is designated as NIH3T3/FGFR-2 and is a recombinant NIH/3T3 cell line carrying the human hKGF receptor.

PC-3 cells were plated in 24-well plates at about $10^5$ cells per well. Following growth for 48–36 hours, the cells were serum starved for 24 hours, washed two times with 500 μl of cold DPBS, and then incubated with 500 μl binding buffer (BB; DPBS, 0.5 mM MgCl$_2$, 0.2% BSA. 0.02% sodium azide) containing various concentrations of $^{125}$I-labeled KGF ranging from 0 to 0.8 nM. Following 3–3.5 hour incubation at 4° C., the binding mixes were aspirated and the well-adhered cells were washed two times with 1 ml BB and once with 1 ml BB supplemented with 0.5M NaCl. The remaining bound labeled hKGF was solubilized in 600 μl 0.5% SDS/0.1M NaOH and counted in a gamma counter (Beckmann). Nonspecific binding was determined in the presence of 100 fold molar excess of unlabeled hKGF. For competition assays, the labeled hKGF was kept constant at 0.3 nM, and varying concentrations of competitor molecules were included in the binding reactions ranging from 0–1,000 nM. Binding curves were fitted to the equation:

[Bound Tracer]=([Total Tracer]*[Receptor])/($K_D$+[Total Tracer])

where [Total Tracer] and [Bound Tracer] were fixed and the $K_D$ and [Receptor] were determined by regression analysis using the software Kaleidagraph (Synergy Software, Reading, Pa.).

NIH3T3/FGFR-2 cells were plated in 24-well plates at about $10^5$ cells per well. Following growth overnight, the cells were serum starved for 1–5 hours, washed two times with 500 μl binding buffer (BB2: serum-free MEM growth medium, 0.1% BSA, 25 mM HEPES, pH 7.4), and then incubated with 250 μl BB2 containing 1 μg/ml heparin (from bovine lung, SIGMA, St. Louis, Mo.), $^{125}$I-labeled hKGF at 0.03 nM, and varying concentrations of competitor molecules (300 nM–0 nM). Following 1 hour incubation at room temperature, the binding mixes were aspirated, and the wells were washed two times with 250 μl cold DPBS and once with 250 μl cold DPBS supplemented with 0.5M NaCl. The bound labeled hKGF was solubilized in 500 μl 0.5% SDS and counted in a scintillation counter (Beckmann).

The inhibition constants (Ki) of the RNA ligands were determined by a nonlinear regression analysis of the data.

Figure 1B:
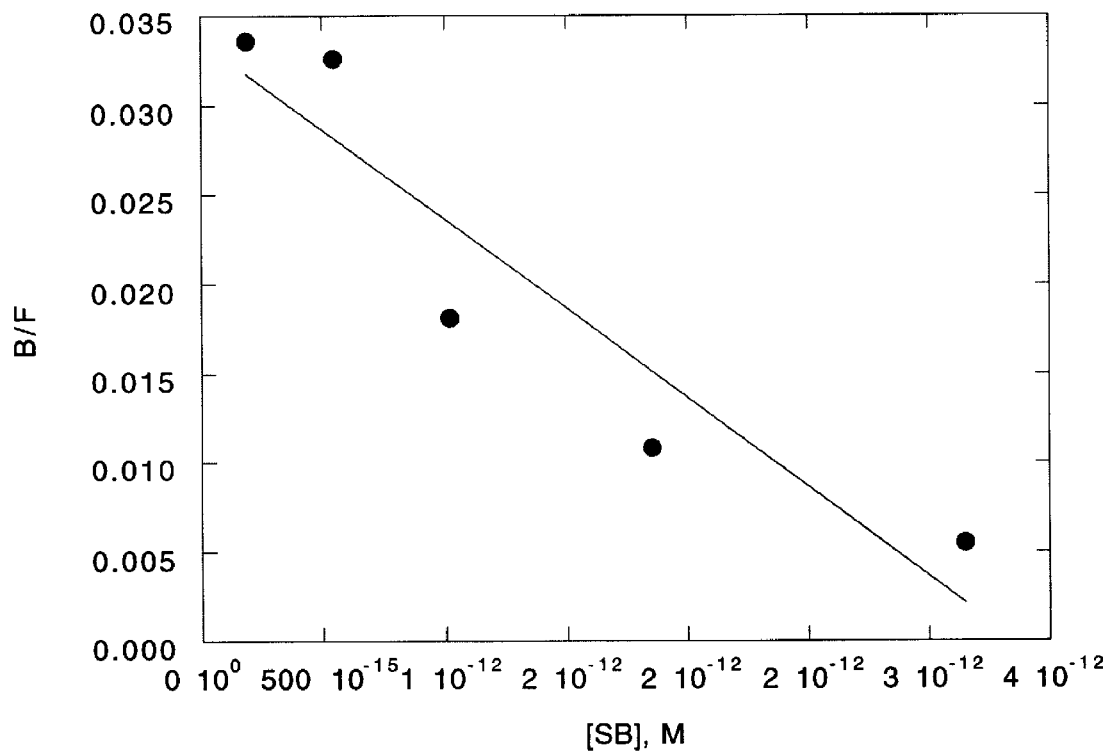
FIG. 1B is the Scatchard analysis of the data points shown in 1A for the SB curve.

In search of KGF receptors on the surface of PC-3 cells, different concentrations of $^{125}$I-hKGF were used, ranging from 0.002 to 0.8 nM, in the presence and absence of 100 fold molar excess of unlabeled hKGF, and saturation binding of the tracer on the surface of PC-3 cells was observed. FIG. 1 shows the plot of the concentration of bound tracer as a function of the total concentration of tracer as well as the Scatchard analysis of the same data. Analysis of the data suggested that there are about 5,000 specific hKGF binding sites per cell with a $K_D$ of 100–200 pM. This $K_D$ is in good agreement with the reported $K_D$ for hKGF of 200 pM (Miki et al., 1992, *Proc natl Acad Sci USA* 89: 246–250).

Figure 2:
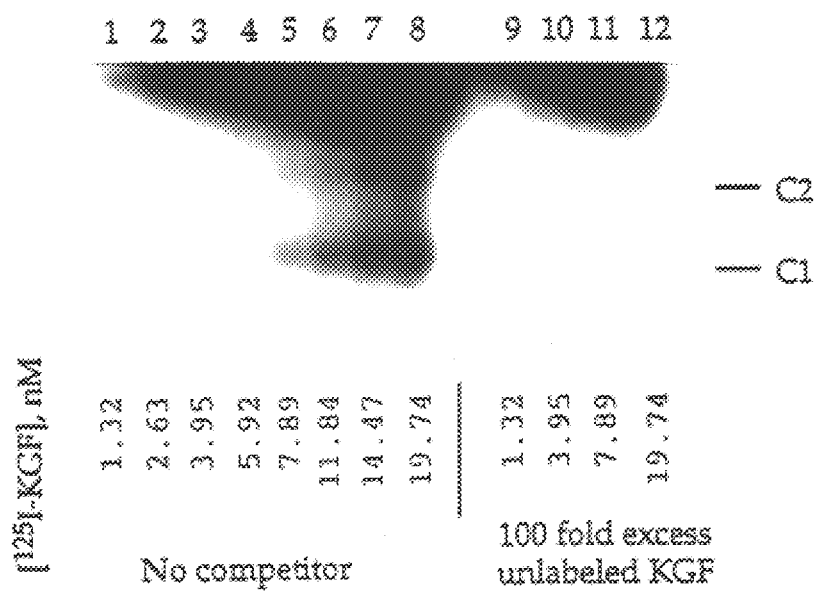
FIG. 2 shows the shift of the electrophoretic mobility due to plasma membrane extracts from PC-3 cells. In lanes 1–8, the membrane extracts were reacted with various concentrations of radiolabeled hKGF as shown under each lane. In addition to the radiolabeled hKGF (as shown under each lane) for lanes 9–12 a 100 fold molar excess was included of unlabeled hKGF. C1 and C2 represent two observed complexes due to the presence of hKGF binding moieties in the PC-3 plasma membrane extracts.

PC-3 plasma membrane extracts were found to alter the electrophoretic mobility (gel shift) of radiolabeled hKGF upon native gel electrophoresis (FIG. 2). For electrophoretic mobility shift gels, about 3×10$^7$ PC-3 cells were gently spun and washed with PBS and then lysed by mixing with equal volume of lysis buffer containing 40 mM Hepes, pH 7.4, 150 mM NaCl, 20% glycerol, 2% triton X-100, 0.1% sodium azide, 3 mM MgCl$_2$, 3 mM EGTA, 2 μM aprotinin, 2 μM leupeptin, 2 mM PMSF, and 400 μM sodium orthovanadate. Following 15 min incubation on ice the extract was spun at 11,000 g at 4° C. for 30 min to remove debris and nuclei and the supernatant was aliquoted and stored at −70° C. For gel analysis, 25 μl binding reactions were set in DPBS, 0.01% HSA, 2 mM MgCl$_2$, containing 3 μl of a 10 fold diluted PC-3 membrane extract in 0.01% HSA, and various concentrations of $^{125}$I-labeled hKGF. Following a 10 min incubation at room temperature, 6X loading dye was added to achieve 1X concentration, and the samples were loaded onto a 5% or 10% native TBE polyacrylamide gel. The gel was prerun at room temperature at 100 Volts. Following loading, the gel was run at 200 Volts for 5 min and then at 100 Volts for 30–60 min at room temperature. The radioactive bands were then visualized by autoradiography. The gel shift of radiolabeled hKGF is not observed in the presence of 100 fold molar excess of unlabeled hKGF (FIG. 2), demonstrating a specific interaction between a component found in the PC-3 membrane extracts and hKGF. The estimated KD from the gel shift experiment is about 8 nM.

In agreement with the competition experiments reported in the literature (Miki et al., *Proc Natl Acad Sci USA* 89: 246–250), gel shift competition curves using unlabeled hKGF and bFGF as well as an unrelated small basic protein namely lysozyme were obtained. Table 8 lists the IC50 values obtained in this experiment. In agreement with previous reports, the data presented in Table 8 show that bFGF competes about 20 fold worse than hKGF for binding with the hKGF receptor present in the PC-3 plasma membrane extracts. The interaction observed by the gel shift appears to be a specific interaction for FGF and it is not due to a charge-charge interaction, as lysozyme, another small positively charged molecule, competes for the PC-3 membrane extract:hKGF complex with about 100 fold worse affinity than hKGF alone.

IC50 values for various RNA ligands obtained with the PC-3 assay are shown in Table 6. A subset of these ligands was tested on the NIH3T3/FGFR-2. Competitive inhibition constants (Ki) were determined from full competition curves and are summarized in Table 7. In determining the Ki values, it was assumed that 3T3 cells have 500,000 binding sites per cell and PC-3 cells have 5,000 binding sites per cell.

The data show that several hKGF ligands can competitively inhibit binding of hKGF to its cell surface receptors. Some of these ligands, such as K14F, have potent competitive activities with Ki's in the low nM range.

This work not only demonstrates that nucleic acid competitors for hKGF were obtained, but also identifies a new assay for screening hKGF competitors including small molecules, antibodies, and peptides. This new assay includes the use of the prostate carcinoma cell line, PC-3. From the data listed in Table 7, it is clear the PC-3 cells behave qualitatively the same as the NIH/3T3 cells transfected with the hKGF receptor. The small quantitative differences observed might be due to different assay conditions and the different number of hKGF receptors expressed in these two cell lines.

EXAMPLE 4. INHIBITION OF THE MITOGENIC ACTIVITY OF KGF

One of the biological effects of KGF is the stimulation of proliferation of epithelial cells (Rubin et al., 1989, *Proc Natl Acad Sci USA* 86: 802–806). This proliferative effect of KGF can be measured by the stimulation of $^3$H-thymidine incorporation in responding cells after exposure to KGF. Three such cell lines have been described before (Rubin et al., 1989, *Proc Natl Acad Sci USA* 86: 802–806) One such cell line designated 4-MBr5 (ATCC# CCL208) was used to determine the effect of ligand K14F on the mitogenic activity of KGF. 4-MBr5 cells grown in F12K containing 30 ng/ml EGF, and 10% FCS, were trypsinized and resuspended in M199 containing 10 mM HEPES, pH 7.4, and 10% FCS at 1.4×10$^5$ cells/ml. A 96-well microtiter plate was seeded with 100 μl of cell suspension and KGF was added at 10 ng/ml (0.5 nM), as well as K14F ligand at various concentrations ranging from 0–1000 nM. Each incubation reaction was set in at least triplicates. Following 24 h incubation at 37° C., $^3$H-thymidine was added at 1 μCi/well along with unlabeled thymidine at 10 nM. The cells were incubated for additional 24 h, the supernatant was aspirated, and the remaining cells were harvested by lysis in 20 μl of 0.2N NaOH. The extent of $^3$H-thymidine incorporation was determined by TCA precipitation and filtration through GFC filter disks (Whattman, Hillsboro, Oreg.). It is clear that ligand K14F completely blocks the mitogenic activity of KGF while random RNA has no effect. In a separate experiment, the anti proliferative bioactivity of ligand K14F was compared to the bioactivity of the neutralized monoclonal antibody MAB251 (R&D Systems, Minneapolis, Minn.) and the two bioactivities were found to be very similar (data not shown). Using nonlinear regression, the data obtained with the 4-MBr 5 cells suggest a Ki value for K14F of about 0.4 nM, which is essentially identical to the Ki value obtained with the PC-3 assay (see Table 7).

TABLE 1

| | |
|---|---|
| Starting RNAs: | |
| 40N7: | |
| 5'GGGAGGACGAUGCGG[-40N-]CAGACGACUCGCCCGA3' | (SEQ ID NO: 1) |
| SELEX PCR Primers: | |
| 5G7: | |
| 5'TAATACGACTCACTATAGGGAGGACGATGCGG3' | (SEQ ID NO: 2) |
| 3G7: | |
| 5'TCGGGCGAGTCGTCTG3' | (SEQ ID NO: 3) |

TABLE 2

Conditions and progress of the SELEX against hKGF

| Round | [RNA], M | [KGF], M | net % bound | Signal/noise | PF[a] | Spin[b] | B-Wash[c] (ml) | U-Wash[d] (ml) | SPKD[e], M | KD$_f$, nM |
|---|---|---|---|---|---|---|---|---|---|---|
| 2'NH2 SELEX | | | | | | | | | | |
| 1 | 1.00E-06 | 3.00E-07 | 4.4 | 11.8 | | | 4 | | 5.61E-06 | 30.0 |
| 2 | 4.00E-06 | 3.00E-07 | 1.5 | 4.2 | | | 5 | | 1.58E-05 | |
| 3 | 1.00E-06 | 1.00E-07 | 5.9 | 20.6 | | | 5 | | 8.52E-07 | |
| 4 | 1.00E-06 | 1.00E-07 | 14.3 | 12.8 | + | | 8 | | 3.21E-06 | 17.0 |
| 5 | 3.00E-07 | 1.00E-08 | 2.5 | 4.5 | + | | 8 | | 7.64E-08 | |
| 6 | 3.70E-08 | 3.70E-09 | 0.7 | 2.6 | + | | 15 | 15 | 3.73E-07 | |
| 7 | 4.10E-09 | 4.10E-10 | 1.1 | 8.2 | + | + | 20 | 20 | 2.46E-08 | 0 7 |
| 8 | 4.60E-10 | 4.60E-11 | 1.5 | 8.8 | + | + | 25 | 25 | 2.04E-09 | 0 3 |
| 9 | 5.10E-11 | 5.10E-12 | 0.7 | 5.9 | + | + | 25 | 25 | 8.76E-10 | |
| 10 | 1.70E-11 | 1.70E-12 | 0.3 | 2.1 | + | + | 25 | 25 | 4.12E-10 | |
| 2'F SELEX | (; | | | | | | | | | |
| 1 | 1.00E-06 | 3.00E-07 | 2.9 | 11.0 | | | 4 | | 3.39E-06 | 300 |
| 2 | 4.00E-06 | 3.00E-07 | 2.2 | 9.9 | | | 5 | | 9.28E-06 | |
| 3 | 3.00E-06 | 3.00E-07 | 5.7 | 5.7 | | | 5 | | 2.15E-06 | |
| 4 | 2.50E-06 | 3.00E-07 | 3.9 | 11.7 | + | | 8 | | 4.98E-06 | 15.0 |
| 5 | 6.70E-07 | 3.00E-08 | 2.3 | 5.8 | + | | 8 | | 3.64E-06 | |
| 6 | 1.20E-08 | 1.23E-09 | 0.3 | 1.8 | + | + | 15 | 15 | 1.59E-07 | |
| 7 | 1.40E-09 | 1.40E-10 | 1.1 | 11.2 | + | + | 20 | 20 | 6.86E-09 | 0.6 |
| 8 | 1.50E-10 | 1.50E-11 | 0.4 | 4.8 | + | + | 25 | 25 | 5.36E-10 | 0.3 |
| 9 | 1.70E-11 | 1.70E-12 | 0.2 | 3.1 | + | + | 25 | 25 | 5.67E-10 | |
| 10 | 1.70E-11 | 1.70E-12 | 0.3 | 3.0 | + | + | 25 | 25 | 1.42E-10 | |

[a]prefiltered RNA through nitrocellulose to counter select for nitrocellulose binding molecules
[b]Brief spinning of the binding reactions
[c]Volume of buffer used to wash the captured complexes
[d]Volume of 0.5 M urea wash following the buffer wash
[e]Calculated single point KD from the binding data at each round
[f]K$_D$ values obtained from binding curves

TABLE 3

Sequences of 2'-NH2 and 2'-F KGF ligands

| Clone | 5' constant | random | 3' constant | SEQ ID NO: |
|---|---|---|---|---|
| 2'-NH2 ligands: | | | | |
| 1N | GGGAGGACGAUGCGG | GAAGGGACGAUAAAGAGGAAUCGAACAACAAGUGGCUGG | CAGACGACUCGCCCGA | 4 |
| 2N | GGGAGGACGAUGCGG | GCGGGAAGGUCCGAAGACCGGCGAAGGAACGAGAAUUGC | CAGACGACUCGCCCGA | 5 |
| 4N | GGGAGGACGAUGCGG | GUGGUGAAGGAAUUGCAAUUGCUAAAGAUACCACGGCC | CAGACGACUCGCCCGA | 6 |
| 6N | GGGAGGACGAUGCGG | GCAGGGAGCAAUGAACUCAAGCCGGUGCACGUGGG | CAGACGACUCGCCCGA | 7 |
| 10N | GGGAGGACGAUGCGG | UAGCUGCUGUCAUGCAAGACACUAGAAGAGAUUAAGAUGGGG | CAGACGACUCGCCCGA | 8 |
| 11N | GGGAGGACGAUGCGG | GGGCCGGAUUUGAACCGACGACUCGGGUUAUGAGCCCGACGU | CAGACGACUCGCCCGA | 9 |
| 14N | GGGAGGACGAUGCGG | UCCAGGGAAUUGAAGUGUCGGGUAGGAACAUAAAGGCGGC | CAGACGACUCGCCCGA | 10 |
| 16N | GGGAGGACGAUGCGG | AAGUUCUAACAAGUUAGUGGAAGGUUCCACUUGAAUGUA | CAGACGACUCGCCCGA | 11 |
| 22N | GGGAGGACGAUGCGG | AUGGAGCUGAAAU | CAGACGACUCGCCCGA | 12 |
| 24N | GGGAGGACGAUGCGG | GUGGGAAGAUGAGCCGGUCGGCAGUAAUGUGACUGCGG | CAGACGACUCGCCCGA | 13 |
| 25N | GGGAGGACGAUGCGG | GAGGGAAUGAGGAAACAACUAGCAGAUAACCGAGCUGGC | CAGACGACUCGCCCGA | 14 |
| 27N | GGGAGGACGAUGCGG | AUGGAGCUGAAAU | CAGACGACUCGCCCGA | 15 |
| 28N | GGGAGGACGAUGCGG | UUGCUCUACAAUGACGGCGGUGACUCCGCAGUUCUUGGACA | CAGACGACUCGCCCGA | 16 |
| 29N | GGGAGGACGAUGCGG | GAGGGGAGAAUGCUAAAUGCAGGAAACAGGCGAAAUGCGUGUGG | CAGACGACUCGCCCGA | 17 |
| 34N | GGGAGGACGAUGCGG | GCGGGAAGCUAAUGGAAGUGGAAUCAGUCACAGUGCGG | CAGACGACUCGCCCGA | 18 |
| 35N | GGGAGGACGAUGCGG | GCUUAGGGAAAUGGUUCUGAGGUGU | CAGACGACUCGCCCGA | 19 |
| 36N | GGGAGGACGAUGCGG | GAAGGGAAACAGGAUAAGACAAGUCGAACAAAGCGAGGUG | CAGACGACUCGCCCGA | 20 |
| 37N | GGGAGGACGAUGCGG | AUGGAGCUGAAAU | CAGACGACUCGCCCGA | 21 |
| 42N | GGGAGGACGAUGCGG | GGAGAGCGUAGACGGGAACAUAGAACGAACAUCAACGCGGC | CAGACGACUCGCCCGA | 22 |
| 43N | GGGAGGACGAUGCGG | GAAGUGGAUAGAACAGUCAGAAAAUGUAAGCGUGAGGUG | CAGACGACUCGCCCGA | 23 |
| 47N | GGGAGGACGAUGCGG | GAAGGGUAGGAAGGUCAAGAGGAAAACAGCCGCUUCGGGGUG | CAGACGACUCGCCCGA | 24 |
| 48N | GGGAGGACGAUGCGG | GGCAAAGGAAGUUGGAAUCGGGACUAAGUAGUGUGUGGC | CAGACGACUCGCCCGA | 25 |
| 54N | GGGAGGAGGAUGCGG | AGAACCAACAGAGCCCCCUGGUGGGGGAAGGAUCU | CAGACGACUCGCCCGA | 26 |
| 55N | GGGAGGACGAUGCGG | ACACACAAGUGAAGGUCAGACGCGAAUUACGUGGGUGGG | CAGACGACUCGCCCGA | 27 |
| 57N | GGGAGGACGAUGCGG | UCGUGGGGUGGGGGGGCAGCGUUGGAAUAAGUAACUGGUAACGGCUGGC | CAGACGACUCGCCCGA | 28 |
| 59N | GGGAGGACGAUGCGG | GGUGGUUGGUUACCUGUAAUUAUAUGAUUCUGGCUUAG | CAGACGACUCGCCCGA | 29 |
| 60N | GGGAGGACGAUGCGG | CCCCUUAGCUCAGUGGUUAGAG | CAGACGACUCGCCCGA | 30 |
| 65N | GGGAGGACGAUGCGG | UAACGUUGGAAUAGGGUUAAACAGCUGGAAAUAACGUAGGUGGC | CAGACGACUCGCCCGA | 31 |
| 69N | GGGAGGACGAUGCGG | GUAGGGAGUAGGACGAACAUAACAGUGCAACCAUCGUGGC | CAGACGACUCGCCCGA | 32 |
| 71N | GGGAGGACGAUGCGG | AAACGGCUGGGCAAAAGUGAGGGGUAGGAUGUACCAUGGGU | CAGACGACUCGCCCGA | 33 |
| 72N | GGGAGGACGAUGCGG | GAGGGGAAAAUGAGACCGACAGAGAUUGACGGAAGUACUGGG | CAGACGACUCGCCCGA | 34 |
| 2'-F ligands: | | | | |
| 2F | GGGAGGACGAUGCGG | GCAUUCGUCAAUACCUGUUUUUAUUCCUUUUCUAGCGGCC | CAGACGACUCGCCCGA | 35 |
| 3F | GGGAGGACGAUGCGG | AUGUAAUGCCACUACUACUUUCGAACCCGCACGUGGC | CAGACGACUCGCCCGA | 36 |
| 5F | GGGAGGACGAUGCGG | CGUCCCGAGUCCAGUCCACUGCUGUCCUGAUAACCUUCUGUUGU | CAGACGACUCGCCCGA | 37 |
| 6F | GGGAGGACGAUGCGG | GAUCCUUUGGCUUCGCCUUGUGACCCCUGCCUUGUCCCCC | CAGACGACUCGCCCGA | 38 |
| 7F | GGGAGGACGAUGCGG | CGGGUACUCUUCUUCGCCAGCUCUCUACUCCAAGCGCACCUGCC | CAGACGACUCGCCCGA | 39 |
| 8F | GGGAGGACGAUGCGG | UUUCGAAUAGGGCUAGAACUAGCUCCAUCUUGGUCCGGUGC | CAGACGACUCGCCCGA | 40 |
| 9F | GGGAGGACGAUGCGG | AUAAUGGCUAGAACUAGUCCUGUCCAUCCUACCCUGGGUGC | CAGACGACUCGCCCGA | 41 |
| 10F | GGGAGGACGAUGCGG | GACCAGUGGCGGAUUUUCAGCAAUCCUCCCCCCUGCC | CAGACGACUCGCCCGA | 42 |
| 11F | GGGAGGACGAUGCGG | UGAUGGCGACCAGUCAAACCGGUCAAACUCUUUACUCCC | CAGACGACUCGCCCGA | 43 |
| 12F | GGGAGGACGAUGCGG | GAAUUAACAGGGCCAGAAUUCUCAUCUCUUCCCGUGACC | CAGACGACUCGCCCGA | 44 |
| 13F | GGGAGGACGAUGCGG | CACCUUAGACCUGUCCCCAAGCGUGAGUUGCUGUUGGCC | CAGACGACUCGCCCGA | 45 |
| 14F | GGGAGGACGAUGCGG | UGGUCUCCAAUUCUAAACUUUCCCAUCGUAUCUGGGC | CAGACGACUCGCCCGA | 46 |

TABLE 3-continued

Sequences of 2'-NH2 and 2'-F KGF ligands

| Clone | 5' constant | random | 3' constant | SEQ ID NO: |
|---|---|---|---|---|
| 15F | GGGAGGACGAUGCGG | UCAUGGUGCUUCCACAGCUCUCCAUGAUCGCCGGC | CAGACGACUCGCCCGA | 47 |
| 16F | GGGAGGACGAUGCGG | GAAUUCCAGCGCUUGACUGAUACAAACNUCCGUGCC | CAGACGACUCGCCCGA | 48 |
| 19F | GGGAGGACGAUGCGG | CAA-NNNNNNCUCUCUGGCGUUCCGCAACCCGCCCC | CAGACGACUCGCCCGA | 49 |
| 20F | GGGAGGACGAUGCGG | AGUAUUCCAGCCUGGAUUCACAUAGUCAGUGCUCUCCGUGCC | CAGACGACUCGCCCGA | 50 |
| 21F | GGGAGGACGAUGCGG | UCCUAGCAGGCGAUUCAUCCCGUUCUCACAGCGUUGCCC | CAGACGACUCGCCCGA | 51 |
| 22F | GGGAGGACGAUGCGG | CCUGAAGUACAGGCUCUAAACUCCAAGCGCGACCGUCGC | CAGACGACUCGCCCGA | 52 |
| 23F | GGGAGGACGAUGCGG | CCCUACCACUUUUUCCCUCUACUGUUAUCCGUCCC | CAGACGACUCGCCCGA | 53 |
| 24F | GGGAGGACGAUGCGG | UGGUCCCUAGAUCUACAGCACUCCAUCGCAUGGGC | CAGACGACUCGCCCGA | 54 |
| 26F | GGGAGGACGAUGCGG | UCAAGCUAACAGUCUGGCAAUGCCAUUAUGGCGCC | CAGACGACUCGCCCGA | 55 |
| 27F | GGGAGGACGAUGCGG | CaGUCUGGAUCUAUUGGAAUUUAGUCCUCAACUGCCC | CAGACGACUCGCCCGA | 56 |
| 28F | GGGAGGACGAUGCGG | GAUUCUUUCGGCAAGUGAAAAUAUCCUGCUUCCGAGC | CAGACGACUCGCCCGA | 57 |
| 29F | GGGAGGACGAUGCGG | GGACUUCAACUAAGUCCCUCAUUUGCUCGCUCCUGUGCC | CAGACGACUCGCCCGA | 58 |
| 31F | GGGAGGACGAUGCGG | AACGGAGAUGUCCCUCAAMAUUUACCGUCUCGUUUGCGCCC | CAGACGACUCGCCCGA | 59 |
| 35F | GGGAGGACGAUGCGG | CGAAAUUAGCUCUUAUGACUCAGUUUCCUUGCGCCC | CAGACGACUCGCCCGA | 60 |
| 37F | GGGAGGACGAUGCGG | GCCCGAUCUACUGCAUUACCGAAACGAUUCCCACUGUG | CAGACGACUCGCCCGA | 61 |
| 38F | GGGAGGACGAUGCGG | NGACUGAUUUUCCUUGNCAGUGUAAUUUCCUGGCUGCC | CAGACGACUCGCCCGA | 62 |
| 41F | GGGAGGACGAUGCGG | GGACUUUGACAGGCAUUGAUUUCGACCGUUCCCGUGCC | CAGACGACUCGCCCGA | 63 |
| 42F | GGGAGGACGAUGCGG | CGACACAAUAGCCUUUGAUCCCAUGAUGGCUCGCUGCC | CAGACGACUCGCCCGA | 64 |
| 43F | GGGAGGACGAUGCGG | UGUAGUUUCCCUGUAUGCAUUCUUUCCAUGCGCACGC | CAGACGACUCGCCCGA | 65 |
| 44F | GGGAGGACGAUGCGG | UCGAGUGUUCUCCCUUCGGUAACUAUUNNNNAUUUGCUGCC | CAGACGACUCGCCCGA | 66 |
| 45F | GGGAGGACGAUGCGG | GUCGUAUUCAUCCCUUGUUCUCUUUCGUUGCACCUGCC | CAGACGACUCGCCCGA | 67 |
| 49F | GGGAGGACGAUGCGG | GGACUUUGACAGGCaUUGAUUUCGACGUUCCCGUUGGC | CAGACGACUCGCCCGA | 68 |
| 50F | GGGAGGACGAUGCGG | UGAUCAAUCGGCGCUUUACUUCUUGCGCUCACCGUGCC | CAGACGACUCGCCCGA | 69 |
| 51F | GGGAGGACGAUGCGG | CAGUCUCCCUAGGUUUCAUUCUCUGCAGCAUUCCGGGUNC | CAGACGACUCGCCCGA | 70 |
| 53F | GGGAGGACGAUGCGG | AUCAAAAGCACUCAUUCCCGUGCUCGCUUCAUUGGUCCC | CAGACGACUCGCCCGA | 71 |
| 54F | GGGAGGACGAUGCGG | AAGAUCUCCCAACUGCUGUGGCUAAUUAAUUCUCUCCGGUCCC | CAGACGACUCGCCCGA | 72 |
| 55F | GGGAGGACGAUGCGG | UCCGUCAUAAACGGCCAUAAACUGGAAUACUCCCGCC | CAGACGACUCGCCCGA | 73 |
| 56F | GGGAGGACGAUGCGG | GGACAAWYAGCGGUGUCUUUUCAUUUNKAUCCUCCGACRUCC | CAGACGACUCGCCCGA | 74 |
| 57F | GGGAGGACGAUGCGG | UGACUAUCUGGCUCGAUCAAUCACCCGAGCCACCGCGC | CAGACGACUCGCCCGA | 75 |
| 58F | GGGAGGACGAUGCGG | GAACUAAUGGCCGUGAUUAACCAAUGCAGGCUUCCUGCC | CAGACGACUCGCCCGA | 76 |
| 60F | GGGAGGACGAUGCGG | UGACAUGGAAUUUCUACGGGCCGAUCCUGCCAGCCGUGUG | CAGACGACUCGCCCGA | 77 |

TABLE 4

Kd values hKGF ligands

| Clone | Kd in nM 1 | 2 | Clone | Kd in nM 1 | 2 |
|---|---|---|---|---|---|
| 1N | 0.51 | | 2F | 1.77 | |
| 2N | 0.77 | | 3F | 4.47 | |
| 4N | 0.75 | | 5F | 2.53 | |
| 6N | 0.71 | | 6F | 0.05 (37) | 3.25 |
| 10N | 1.10 | | 7F | 3.69 | |
| 11N | 1.28 | | 8F | 2.63 | |
| 14N | 0.44 | | 9F | 0.83 | |
| 16N | 1.40 | | 10F | 0.47 | |
| 22N | 5.70 | | 11F | 3.74 | |
| 24N | 1.16 | | 12F | 1.38 | |
| 25N | 0.87 | | 13F | 0.03 (28) | 3.39 |
| 27N | ND | | 14F | 0.006–0.03 (25–44) | 0.94–2.57 |
| 28N | 2.54 | | 15F | 0.07 (33) | 8.70 |
| 29N | 0.43 | | 16F | 0.83 (49) | 44.8 |
| 34N | 0.80 | | 19F | 1.6 | |
| 35N | 2.32 | | 20F | 2.05 | |
| 36N | 8.27 | | 21F | ND | |
| 37N | ND | | 22F | 2.75 | |
| 42N | 0.78 | | 23F | 2.52 | |
| 43N | 0.79 | | 24F | 2.02 | |
| 47N | 1.76 | | 26F | 0.23 (43) | 2.55 |
| 48N | 1.34 | | 27F | 1.52 | |
| 54N | 5.35 | | 28F | ND | |
| 55N | 1.25 | | 29F | 3.24 | |
| 57N | 35.8 | | 31F | 1.0 | |
| 59N | 22.0 | | 35F | 1.1 | |
| 60N | 7.38 | | 37F | 0.46 | |
| 65N | 26.56 | | 38F | 0.33 | |
| 69N | 15.20 | | 41F | 1.44 | |
| 71N | 3.52 | | 42F | 0.9 | |
| 72N | 7.67 | | 43F | 1.13 | |
| random | 30 | | 44F | 1.32 | |
| | | | 45F | 4.7 | |
| | | | 49F | 1.0 | |
| | | | 50F | 0.12 (21) | 2.10 |
| | | | 51F | 1.27 | |
| | | | 53F | 0.70 | |
| | | | 54F | 1.23 | |
| | | | 55F | 2.52 | |
| | | | 56F | 0.07 (32) | 3.00 |
| | | | 57F | 1.20 | |
| | | | 58F | 2.52 | |
| | | | 60F | 2.10 | |
| | | | random | 30 | |

For biphasic curves, Kd1 is for the high affinity component. Number in parentheses indicate the per cent of the high affinity component.

TABLE 5

Binding Specificity of the 2'-F Ligand K14F

| Target | Ratio: $K_D$ Target/$K_D$ hKGF |
|---|---|
| human hKGF | 1 |
| rat hKGF | 1,254 |
| human aFGF | 38,650 |
| human bFGF | 1,071 |
| human PDGF | 432 |

The ratios shown are averages of at least two determinations

TABLE 6

$IC_{50}$ values from the PC-3 assay

| Competitor | IC50, nM |
|---|---|
| hKGF | 70 |
| Heparin, 5,000 | 30 |
| 40N7F | >1000 |
| K6F | 4 |
| K13F | 30 |
| K14F | 10 |
| K15F | 20 |
| K56F | 1 |
| K10F | 30 |
| K37F | 20 |
| K38F | 0.6 |
| K43F | 80 |
| 40N7N | >1000 |
| K1N | 50 |
| K2N | 200 |
| K4N | 70 |
| K6N | 80 |
| K14N | 6 |
| K29N | 40 |
| K42N | 800 |
| K43N | 800 |

TABLE 7

Ki values of hKGF competitors on the PC3 and NIH3T3/FGFR-2 competition assay

| Cell line | Competitor | Ki, nM | R | |
|---|---|---|---|---|
| PC-3 | hKGF | 7.700 | 0.95519 | |
| | 2'F random | 930.000 | 0.99713 | |
| | 2'NH$_2$ random | 673.000 | 0.85357 | |
| | Hep5000 | 6.500 | 0.99984 | |
| | K14F | 0.200 | 0.97735 | |
| | K6F | 0.160 | 0.95927 | |
| | K38F | 0.220 | 0.99013 | |
| | K56F | 0.160 | 0.95927 | |
| | K14N | 1.400 | 0.94698 | |
| NIH3T3/FGFR-2 | hKGF | 0.034 | 0.9933 | |
| | 2'F random | >10,000.000 | | |
| | 2'NH$_2$ random | >10,000.000 | | |
| | Hep5000 | 26.300 | 0.97856 | partial comp. |
| | K14F | 2.700 | 0.99047 | |
| | K6F | 6.800 | 0.96202 | |
| | K38F | 20.000 | 0.98659 | |
| | K56F | 27.400 | 0.97582 | |
| | K14N | 10.600 | 0.97856 | partial comp. |

TABLE 8

IC50 values obtained with the gel shift assay

| Competitor | IC50, nM |
|---|---|
| KGF | 70 |
| bFGF | 1,500 |
| Lysozyme | 10,000 |

We claim:

1. A method of identifying nucleic acid ligands to Human Keratinocyte Growth Factor (hKGF), comprising:

a) preparing a candidate mixture of nucleic acids;

b) contacting the candidate mixture of nucleic acids with hKGF, wherein nucleic acids having an increased affinity to hKGF relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acid sequences with relatively higher affinity and specificity for binding to hKGF, whereby nucleic acid ligands of hKGF may be identified.

2. The method of claim 1 further comprising:

e) repeating steps b), c), and d).

3. The method of claim 1 wherein said candidate mixture of nucleic acids is comprised of single stranded nucleic acids.

4. The method of claim 3 wherein said single stranded nucleic acids are ribonucleic acids.

5. The method of claim 4 wherein said nucleic acids are 2'-amine (2'—$NH_2$) modified ribonucleic acids.

6. The method of claim 4 wherein said nucleic acids are 2'—F modified ribonucleic acids.

* * * * *